United States Patent
Schermerhorn et al.

(10) Patent No.: US 8,070,205 B2
(45) Date of Patent: Dec. 6, 2011

(54) HARNESS ASSEMBLY FOR A DUAL-MODE TAILGATE

(75) Inventors: John M. Schermerhorn, Columbus, OH (US); Hung V. Phan, Powell, OH (US)

(73) Assignee: Honda Motor Co., Ltd., Tokyo (JP)

( * ) Notice: Subject to any disclaimer, the term of this patent is extended or adjusted under 35 U.S.C. 154(b) by 0 days.

(21) Appl. No.: 12/783,003

(22) Filed: May 19, 2010

(65) Prior Publication Data
US 2010/0225134 A1    Sep. 9, 2010

(51) Int. Cl.
*B62D 33/03* (2006.01)
*H01B 17/58* (2006.01)

(52) U.S. Cl. .......... 296/26.11; 296/208; 174/152 G; 174/650

(58) Field of Classification Search .......... 296/26.11, 296/146.1, 146.7, 146.5, 50, 37.7, 57.1, 106; 174/72 A, 650; 439/34, 607, 501, 502, 507; B62D 33/03; H01B 17/58
See application file for complete search history.

(56) References Cited

U.S. PATENT DOCUMENTS

| | | | |
|---|---|---|---|
| 7,053,304 B2 * | 5/2006 | Ojima et al. | 174/72 A |
| 7,304,239 B1 | 12/2007 | Harris et al. | |
| 7,306,481 B2 | 12/2007 | Tsukamoto | |
| 7,408,115 B2 | 8/2008 | Doring | |
| 7,423,224 B2 * | 9/2008 | Puhl | 174/650 |
| 7,484,784 B2 | 2/2009 | Ohly | |
| 7,533,920 B2 | 5/2009 | Ohly | |
| 2002/0113460 A1 * | 8/2002 | Murakami et al. | 296/152 |
| 2002/0151213 A1 * | 10/2002 | Aoki et al. | 439/502 |
| 2005/0148212 A1 * | 7/2005 | Ojima et al. | 439/34 |
| 2006/0038099 A1 * | 2/2006 | Kalinowski | 248/231.81 |
| 2007/0222230 A1 * | 9/2007 | Plett et al. | 292/99 |
| 2009/0095858 A1 * | 4/2009 | Katou et al. | 248/205.1 |

FOREIGN PATENT DOCUMENTS
JP    2005014643    9/2008
* cited by examiner

*Primary Examiner* — Glenn Dayoan
*Assistant Examiner* — Sunsurraye Westbrook
(74) *Attorney, Agent, or Firm* — Rankin Hill & Clark LLP

(57) ABSTRACT

A harness assembly for a vehicle is provided. The vehicle includes a body and a dual-mode tailgate connected to the body via a dual-action hinge. The harness assembly includes a protector connected to a frame of the tailgate. The protector has a body shaped to conform to a first portion of the tailgate frame having a first contour and a second portion of the tailgate frame having a second differing contour. A portion of the protector body is configured to route a section of a tailgate harness adjacent an outboard lateral edge of the tailgate frame and past the section of the tailgate harness under a dual-action hinge.

18 Claims, 7 Drawing Sheets

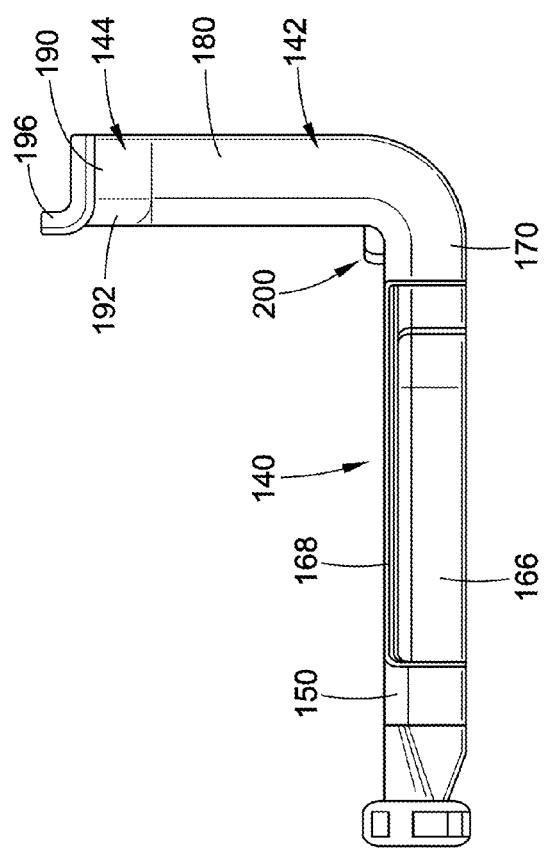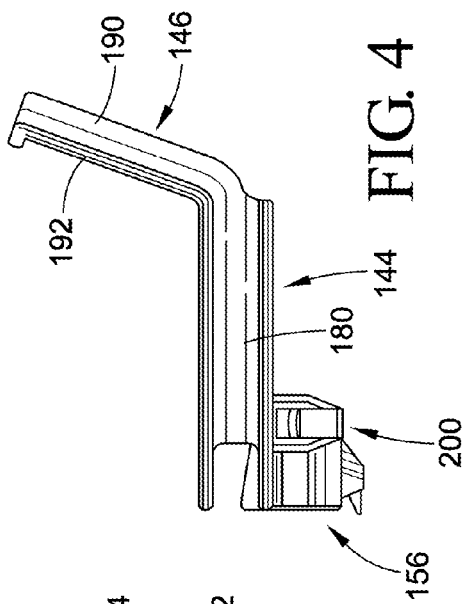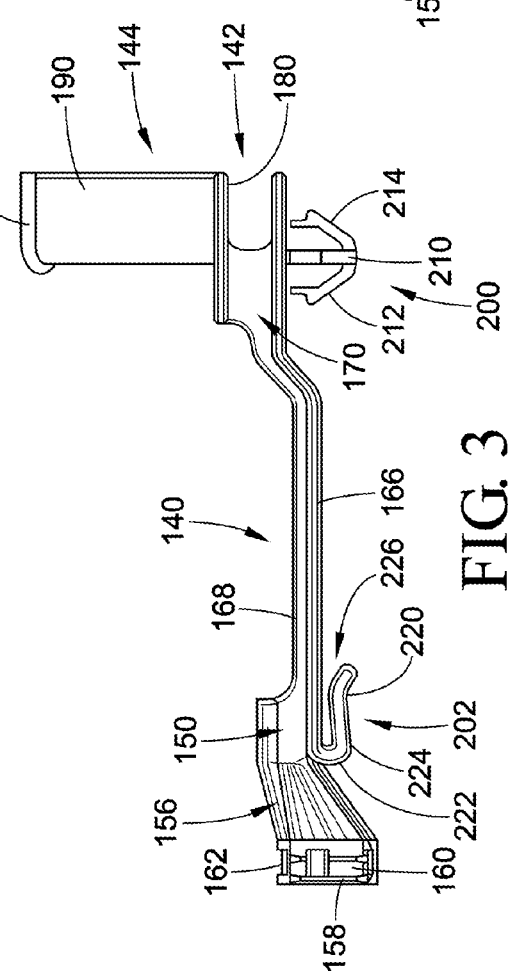

HARNESS ASSEMBLY FOR A DUAL-MODE TAILGATE

BACKGROUND

Exemplary embodiments herein generally relate to a harness assembly for a vehicle having a load-carrying bed, and, more particularly, to a harness assembly for passing a wire harness from a vehicle body to a dual-mode tailgate.

Dual-mode tailgates for vehicles having a load-carrying bed are generally known. "Dual-mode" refers to the two directions or pivot axes along which the dual-mode tailgate is openable. More particularly, a dual-mode tailgate includes a dual-action hinge which allows the tailgate to be selectively openable in a first, fold-down direction about a first axis generally parallel with a bottom edge of the tailgate similar to the conventional tailgate. The dual-action hinge also allows the tailgate to be selectively openable in a second, side-to-side direction about a second axis generally parallel with a lateral edge of the tailgate.

Known vehicles having the dual-action hinge for a tailgate typically pass a wire harness or wires from the vehicle body to the tailgate through a large rubber grommet. The rubber grommet requires a large body section to secure it to the vehicle body. Additionally, the rubber grommet inflates the wire bundle diameter, which, in turn, requires a large clearance area during operation of the tailgate in both the first, fold-down direction and the second, side-to-side direction. As such, the current method for routing a wire harness through a dual-action hinge either has a significant impact to the surrounding parts and/or is not reliable enough for safety related functionality.

BRIEF DESCRIPTION

According to one aspect, a harness assembly for a vehicle is provided. The vehicle includes a body and a dual-mode tailgate connected to the body via a dual-action hinge. The harness assembly comprises a protector connected to a frame of the tailgate. The protector has a body shaped to conform to a first portion of the tailgate frame having a first contour and a second portion of the tailgate frame having a second differing contour. A portion of the protector body is configured to route a section of a tailgate harness adjacent an outboard lateral edge of the tailgate frame and past the section of the tailgate harness under a dual-action hinge.

According to another aspect, a harness assembly for a vehicle including a body and a dual-mode tailgate connected to the body via a dual-action hinge comprises a protector configured to route a tailgate harness from the tailgate under the dual-action hinge and to the vehicle body. The protector has a body including a first section laterally spaced from and extending generally parallel to an outboard lateral side of a frame of the tailgate and a second section extending generally perpendicular to the first section. Each of the first and second sections includes a channel portion for receiving the tailgate harness.

According to yet another aspect, a vehicle comprises a body, a dual-mode tailgate having a frame, a dual-action hinge configured to connect the dual-mode tailgate to the body, and a protector configured to route a tailgate harness from the tailgate under the dual-action hinge and to the vehicle body. The protector includes a body including a first section, a second section and a third section. The first section is laterally spaced from and extends generally parallel to an outboard lateral side of the frame of the tailgate. The second section extends generally perpendicular to the first section. The third section extends angularly from the second section. The protector includes a first attachment member and a second differing attachment member for mounting the protector to the tailgate frame.

BRIEF DESCRIPTION OF THE DRAWINGS

FIG. 2 is a top plan view of the protector of FIG. 1.

FIG. 3 is a front elevational view of the protector of FIG. 1.

FIG. 4 is a side elevational view of the protector of FIG. 1.

DETAILED DESCRIPTION

Figure 1:
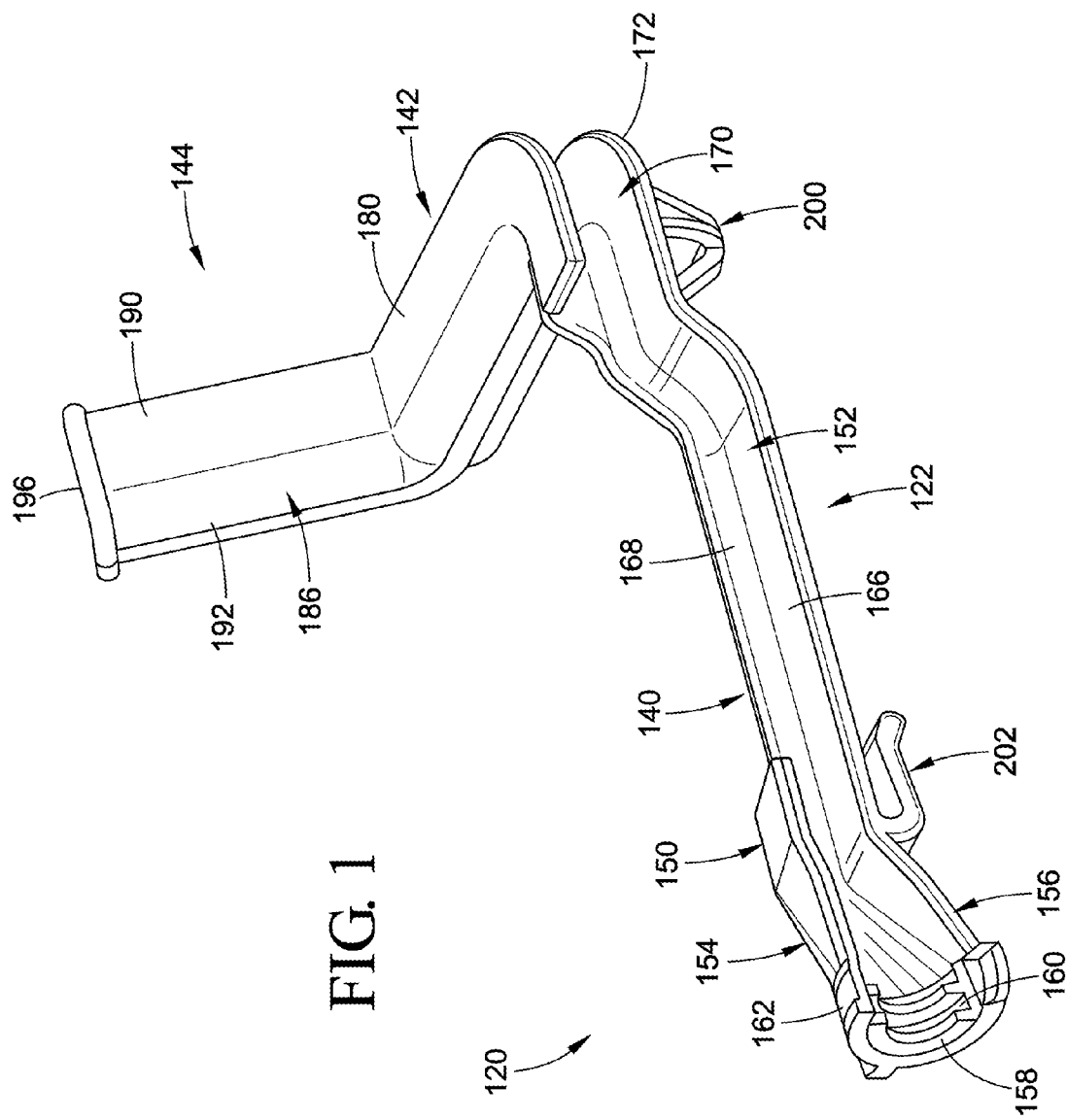
FIG. 1 is a perspective view of an exemplary protector for a harness assembly according to the present invention.

It should, of course, be understood that the description and drawings herein are merely illustrative and that various modifications and changes can be made in the structures disclosed without departing from the present disclosure. All references to direction and position, unless otherwise indicated, refer to the orientation of the tailgate illustrated in the drawings and should not be construed as limiting the claims appended hereto. Like numerals refer to like parts throughout the several views.

Figure 7:
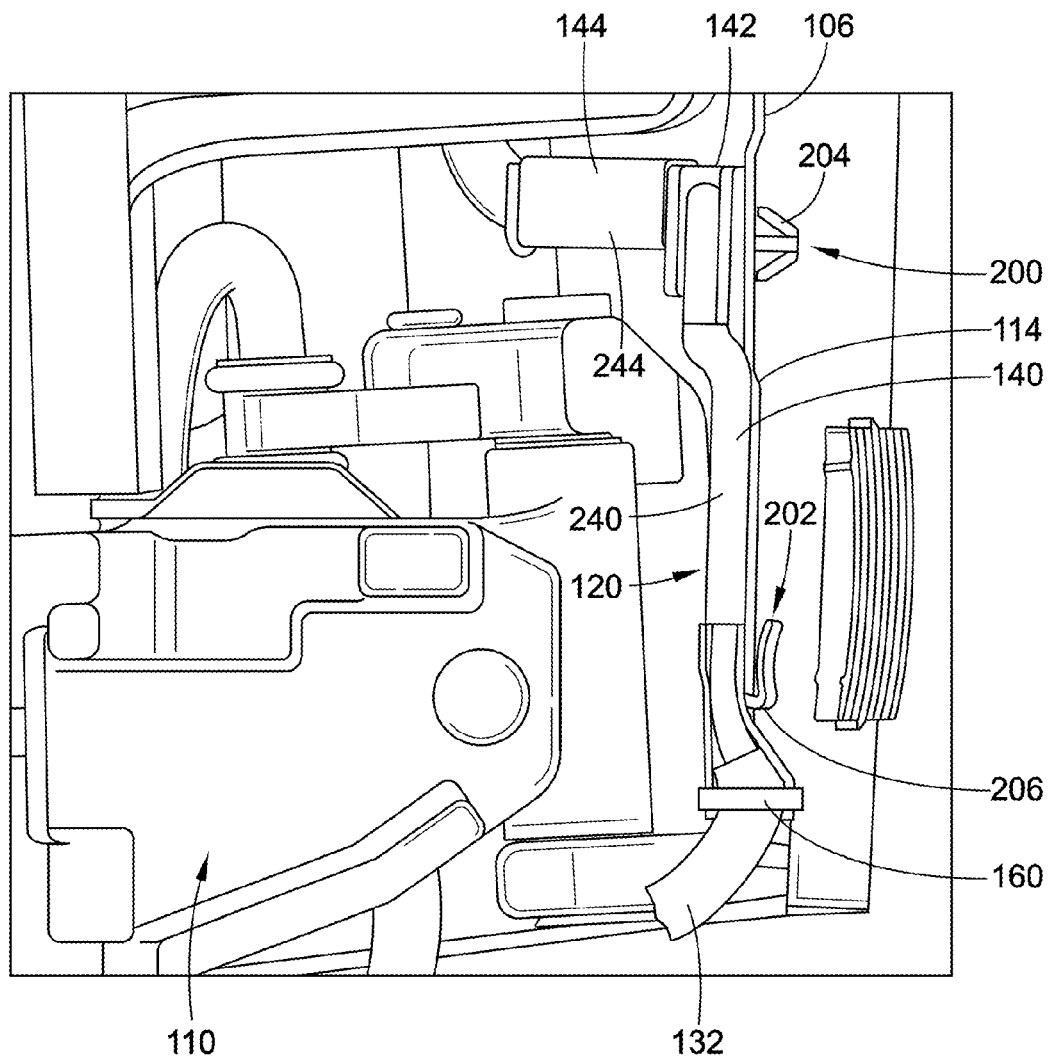
FIG. 7 is an enlarged schematic view showing the protector of FIG. 1 being mounted to the tailgate frame and routing the tailgate wire harness under the dual-action hinge.
Figure 8:
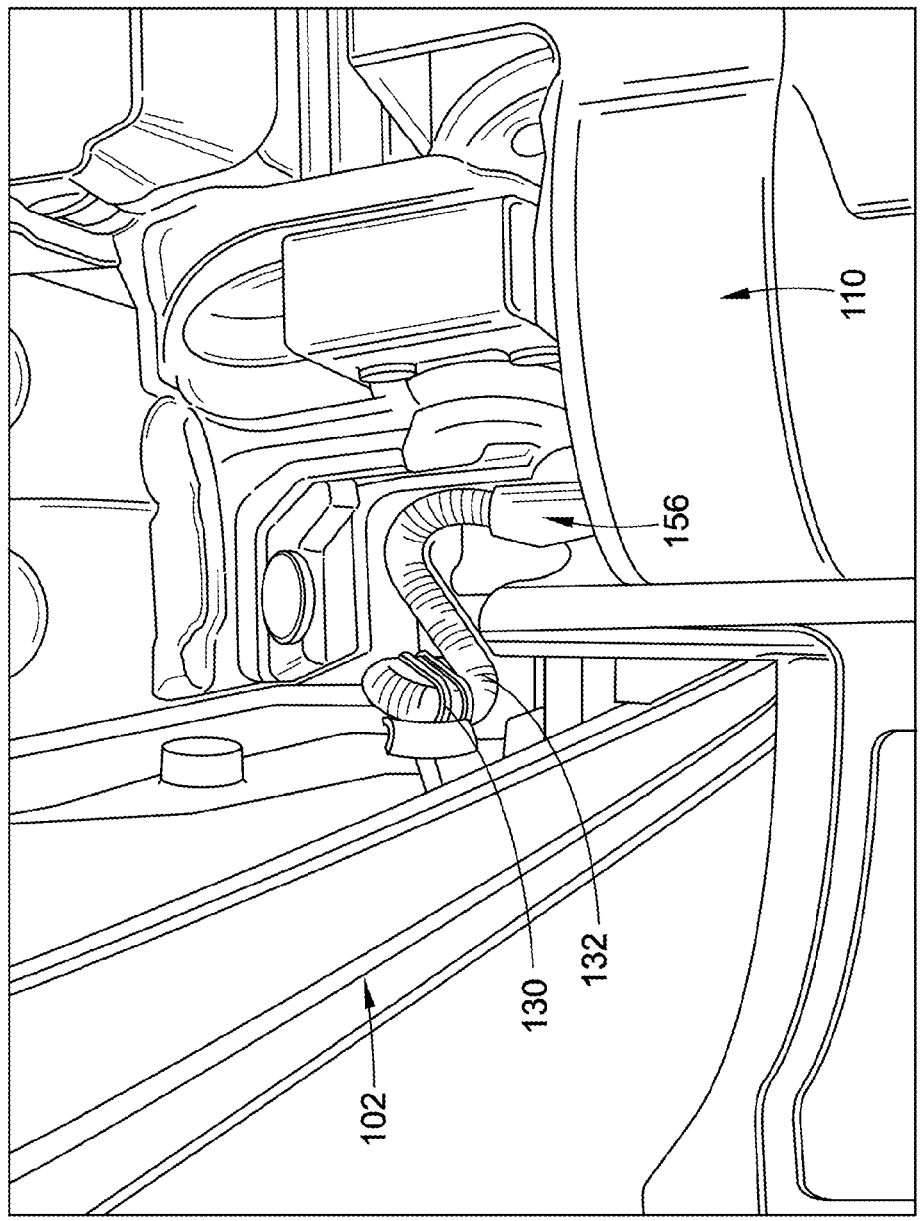
FIG. 8 is an enlarged schematic view of the tailgate of FIG. 6, the exemplary harness assembly further including a corrugated tube for routing the wire harness between the tailgate and the vehicle body and a clip connected to the vehicle body for connecting the wire harness thereto.
Figure 9:
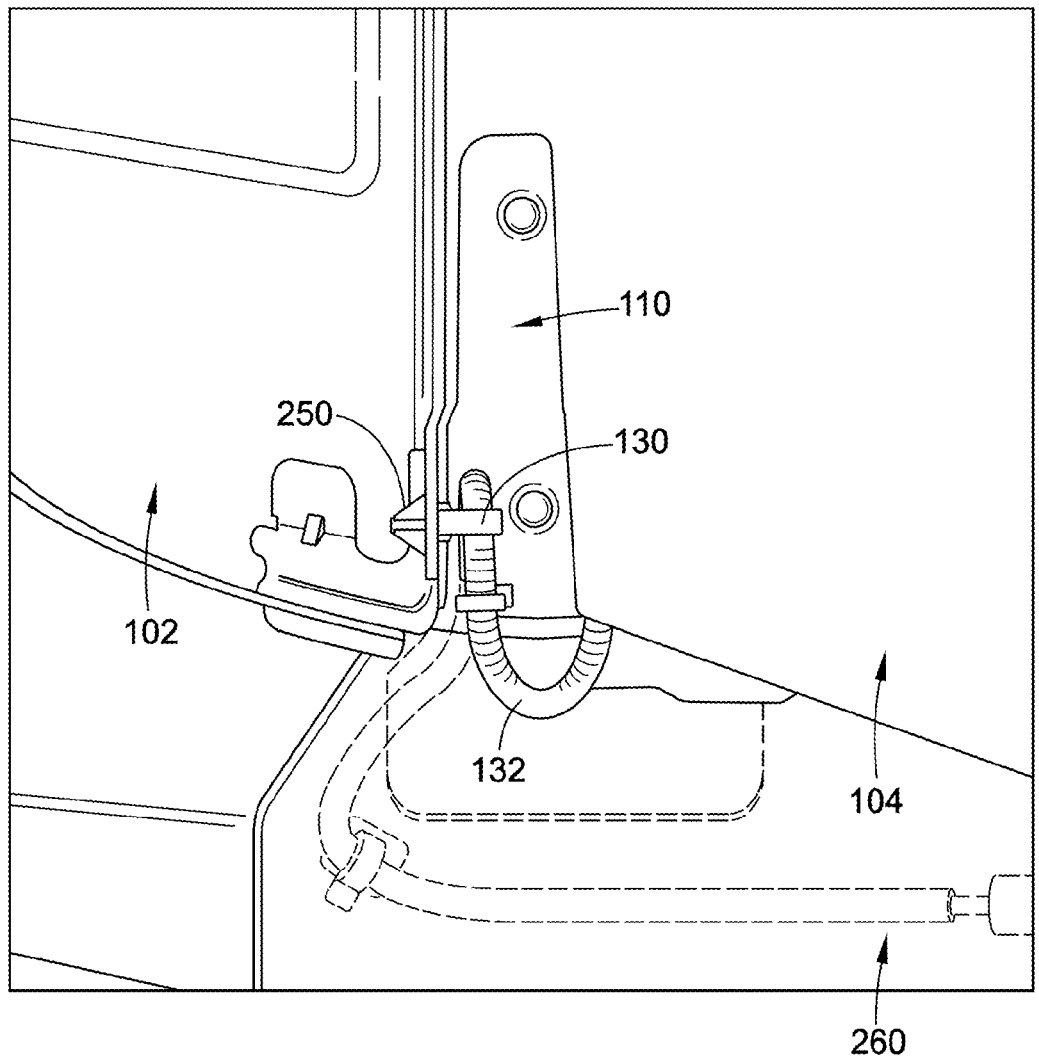
FIG. 9 is a schematic view of the tailgate of FIG. 5 in a swung open position.

Referring now to FIGS. 1-9, an exemplary harness assembly 100 for a vehicle according to the present disclosure is illustrated. The depicted vehicle includes a body 102 and a dual-mode tailgate 104 connected to the body via a dual-action hinge 110. As indicated previously, the dual-mode tailgate is selectively openable in a first, fold-down direction about a first axis generally parallel with a bottom edge of the tailgate (FIG. 6) and a second, side-to-side direction about a second axis generally parallel with a lateral edge 114 of the tailgate (FIG. 9). The dual-action hinge pivotally connects the tailgate, along the first and second axes, to the vehicle body 102. The harness assembly 100 is configured to route a wire harness 112 from the body 102 to the tailgate 104 with little impact to the vehicle body and tailgate.

The exemplary harness assembly 100 comprises a protector 120, an attachment device 130 and an elongated sleeve or tube 132. The protector 120 is connected to a frame 106 of the tailgate 104 adjacent the outboard lateral edge 114 of the tailgate frame 106. The protector 120 includes a body 122 configured to route a section of the tailgate wire harness 112 adjacent to the outboard lateral edge 114 and pass the tailgate wire harness 112 under the dual-action hinge 110. The separate attachment device 130 is mounted to the vehicle body 102 and is configured to route the wire harness 112 along the vehicle body. The elongated sleeve or tube 132 is positioned between the vehicle body and tailgate and receives a portion of the tailgate harness 112 extending between the protector 120 and the attachment device 130. As shown, the exemplary tube 132 is a slit-less corrugated tube having excellent abrasion resistance which protects the tailgate harness 112 from damage due to debris located within a load-carrying bed (not shown) of the vehicle.

With particular reference to FIGS. 1-4, the protector body 122 includes three separate sections, namely a first section 140, a second section 142 and a third section 144. In the depicted exemplary embodiment, the first section 140 includes a first channel portion 150, a second channel portion 170 and a low-profile portion 152 which is located between the first and second channel portions. The first channel portion 150 is generally U-shaped and is located at an end 154 of the first section 140. The first channel portion 150 includes an enlarged or flared section 156 which is canted downwardly relative to the low-profile portion 152 for receiving an end of the corrugated tube 132. A pair of spaced apart C-shaped projections 158 are provided on an inner surface of the flared section 156. The projections 158 define a recess 160 therebetween for receiving an end portion of the corrugated tube 132 (FIG. 7). A groove 162 is provided on an outer surface of the enlarged section 156. The groove 162 is configured to receive a fastener, such as a zip tie 164 (FIG. 5), which secures an end of the corrugated tube 132 within the first channel portion 150. This allows the tailgate wire harness 112 to be fed directly into the corrugated tube 132 as the wire harness leaves the protector 120 and extends toward the vehicle body 102. The low-profile portion 152 is generally L-shaped and includes a planar section 166 and a lip 168. In the exemplary embodiment, the lip 168 extends outwardly from the planar section along the entire length of the planar section; although, this is not required. The lip has a height less than a height of the first channel portion 150 which allows the low-profile portion to be positioned under the dual-action hinge 110. The second channel portion 170 is also generally U-shaped and is slightly elevated relative to the low-profile portion 152. The second channel portion 170 is connected the second section 142.

The second section 142 of the protector body 122 extends generally perpendicular from the first section 140. The second section 142 includes a generally U-shaped channel portion 180. As shown, the channel portion 180 extends along the entire length of the second section 142; although, this is not required. The third section 144 of the protector body 122 extends angularly from the second section 142. In the depicted exemplary embodiment, the third section 144 is oriented generally perpendicular to both the first section 140 and the second section 142. The third section 144 includes a low-profile portion 186, which similar in shape to low-profile potion 152. Particularly, the low-profile portion 186 is generally L-shaped and includes a planar section 190 and a lip 192 which extends outwardly from the planar section. The lip 192 extends along the entire length of the planar section 190; although, this is not required. A bead 196 is provided on an end of the third section 144 along both the planar section 190 and the lip 192.

Figure 6:
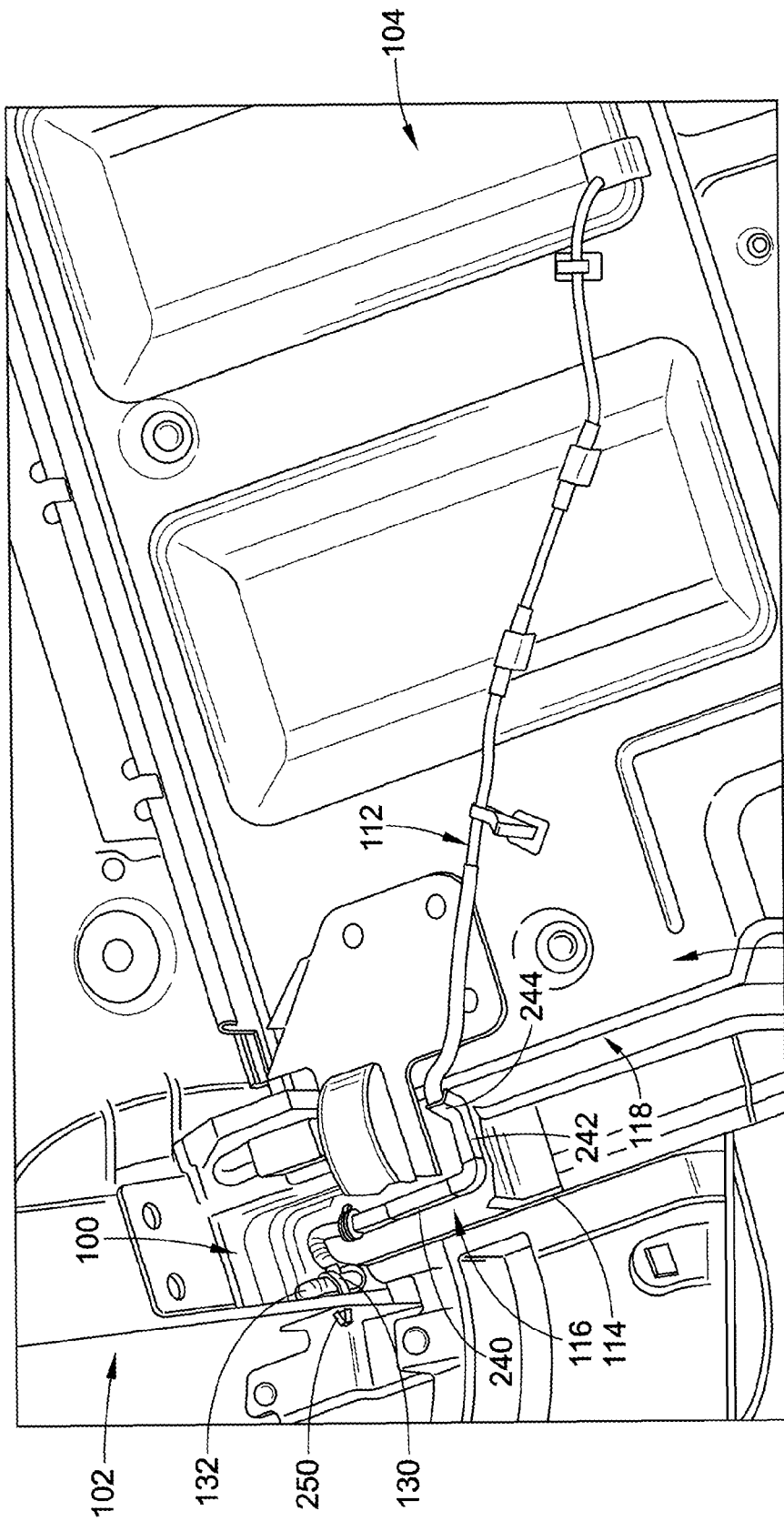
FIG. 6 is a schematic view, partial broken away, of the tailgate of FIG. 5 in a fold-down position.

As shown in FIG. 6, the orientation of the first, second and third sections 140, 142, 144 of the protector body 122 allows the protector body to conform to a first portion 116 of the tailgate frame 106 having a first contour and a second portion 118 of the tailgate frame having a second differing contour (e.g., the second portion 118 extends outwardly from the first portion 116 to define a raised section of the tailgate frame 106). The protector 120 is mounted to the first portion 116 of the tailgate frame 106. Once mounted, the first section 140 is spaced from and extends generally parallel to the outboard lateral side 114 of the tailgate frame 106. The second section 142 extends generally perpendicular to the outboard lateral side 114. The third section 144 extends upwardly from the first portion 116 and generally parallel to a plane defined by the second portion 118 of the tailgate frame 106.

With continued reference to FIGS. 1-4, the protector 120 further includes at least one attachment member for mounting the protector to the tailgate frame 106. In the depicted exemplary embodiment, the protector 120 includes a first attachment member 200 located adjacent the second channel portion 170 and a second attachment member 202 located adjacent the first channel portion 150. As shown, the first attachment member 200 is generally clip-shaped for insertion through an opening 204 (FIG. 7) located on the tailgate frame 106. Particularly, the first attachment member 200 includes an arm 210 and at least one spring-biased finger connected to one end of the arm. As shown, first and second spring-biased fingers 212, 214 are provided on the arm 210. The first and second fingers 212, 214 are biased away from the other end of the arm and can be deflected towards the arm as the first attachment member 200 is inserted through the opening 202 of the tailgate frame 106. Once the first attachment member 200 is fully inserted through the opening 204, the first and second fingers 212, 214 spring away from the arm 210 thereby securing the first attachment member 200 to the tailgate frame 106.

The second attachment member 202 is generally hooked-shaped and is mounted to a bottom edge 206 of the tailgate frame 106. Particularly, the second attachment member 202 includes an arm 220 having an arcuate portion 222 connected to the planar portion 166 of the low-profile section 152 and an engagement portion 224 which extends generally parallel to the planar portion 166. The arcuate portion 222 spaces the engagement portion 224 a predetermined distance from the planar section 166 to define a slot 226 for receiving the edge 206 of the tailgate frame 106. An end of the engagement portion 224 is flared outwardly which allows for ease of insertion of the bottom edge 206 into the slot 226 of the second attachment member 202.

Figure 5:
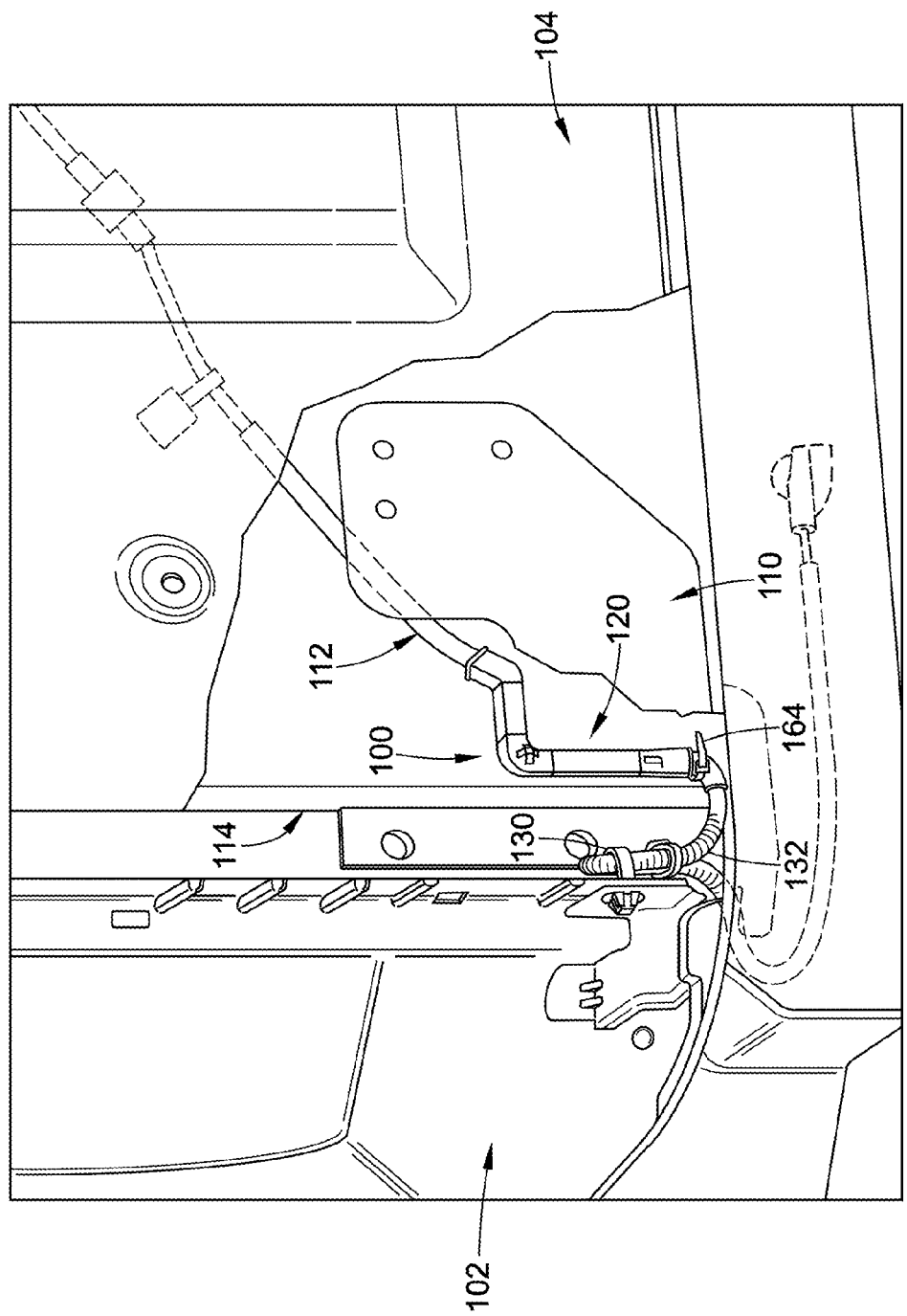
FIG. 5 is a schematic view of a dual-mode tailgate connected to a vehicle body via a dual-action hinge, the tailgate being in a closed position. The protector of FIG. 1 being connected to a frame of the tailgate and the harness assembly routing a wire harness from the tailgate under the dual-action hinge and to the vehicle body.

The use of the harness assembly 100 for the vehicle including the dual-mode tailgate 104 connected to the body 102 via the dual-action hinge 110 will now be described with reference to FIGS. 5-9. As shown in FIGS. 5 and 6, to facilitate the dual-mode action of the tailgate 104, the dual-action hinge 110 attaches to the tailgate frame 106 at a corner thereof formed at the intersection of the bottom edge 206 and the outboard lateral edge 114 of the tailgate. The first and second attachment members 200, 202 mount the protector 120 to the tailgate from in the manner described above. In the mounted position, the first and second sections 140, 142 of the protector 120 are located on the first portion 116 of the tailgate frame 106 and the third section 144 is located on the second portion 118 of the tailgate frame 106. The wire harness 112 is routed along the tailgate frame 106 between the tailgate frame and skin or cladding towards the protector 120. The tailgate harness 112 is routed through the protector 120 under the dual-action hinge 110 and towards the vehicle body 102. The wire harness 112 lies against the planar portions 166, 190 of the first and third sections 140, 144 and is received in the channel portions 150, 170, 180 of the first and second sections 140, 142. Covers 240, 242, 244 can be provided to further protect the tailgate harness 112 as it is routed through the protector 120. Particularly, cover 240 is provided over the low-profile portion 152 of the first section 140. Cover 242 is provided over the channel portion 180 of the second section 142, and cover 244 is provided over the low-profile portion 186 of the third section 144.

As shown in FIGS. 6 and 7, the first section 140 is laterally spaced from and extends generally parallel to the outboard lateral side 114 of the tailgate frame 106 and passes the tailgate harness 112 under the dual-action hinge 110. The first and second attachment members 200, 202 mount the protector 200 at least partially under the dual-action hinge 110. In the low-profile portions 152, 186, the wire harness 112 generally extends along the lips 168, 186. The planar portion 152 lies against the first section 116 of the tailgate frame 106 and the planar portion 190 lies against the second section 118 of the tailgate frame. As shown in FIG. 8, the tailgate harness 112 is received in the slit-less corrugated tube 132, which protects the tailgate harness from damage as the tailgate harness 112 spans between the tailgate 104 and the vehicle body 102. The attachment device 130 is connected to the vehicle body 102. In the depicted exemplary embodiment, the attachment device 130 includes an attachment member 250 similar in structure to first attachment member 200. The attachment member 250 is received in an opening located in the vehicle body 102 for securing the attachment device 130 thereto. The tailgate harness 112 makes a U-turn within the attachment device 130 once it is secured to the vehicle body 102 so that the tailgate harness 112 can be passed easily to a main body harness 260 (FIG. 9) without a large grommet hole.

As is evident from the foregoing, the tailgate wire harness 112 is routed under the dual-action hinge 110 via the harness assembly 100. The protector 120 includes the body 122 having the first section 140, the second section 142 and the third section 144. Each section 140,142 defines a channel portion 150,170,180 for receiving the wire harness. First and second attachment members 200,202 are provided on the protector 120 for mounting the protector to the tailgate frame 106. The attachment of the protector 120 allows the harness protector 120 to be secured in a limited space between the tailgate frame 106 and the tailgate skin or cladding. The first section 140 of the protector body routes the wire harness 112 under the dual-action hinge 110. The second section 142 of the protector body 122 directs the wire harness 112 away from the dual-action hinge 110 and under the tailgate cladding, such that the wire harness is routed between the tailgate frame and the cladding.

With the harness assembly 100, there is little impact to the surrounding parts of the vehicle (e.g., the body 102 and tailgate 104) and there is increased reliability. It should be appreciated that the portion of the wire harness 112 spanning between the vehicle body 102 and tailgate 104 and located within the corrugated tube 132 can be insulated with a polyethylene. The polyethylene insulation on the wire harness 112 keeps the wire harness from becoming brittle in cold weather and provides superior bending durability.

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A harness assembly for a vehicle including a vehicle body and a dual-mode tailgate connected to the vehicle body via a dual-action hinge configured to allow the tailgate to be selectively openable in a first, fold-down direction and a second, side-to-side direction, the harness assembly comprising:
a protector connected to a frame of the tailgate, the protector having a protector body shaped to conform to a first portion of the tailgate frame having a first contour and a second portion of the tailgate frame having a second differing contour, the protector body including a first section, a second section extending generally perpendicular from the first section and a third section extending from the second section and oriented generally perpendicular to both the first section and the second section, the protector body being configured to route a section of a tailgate harness adjacent an outboard lateral edge of the tailgate frame and pass the section of the tailgate harness under a dual-action hinge.

2. The harness assembly of claim 1, wherein each of the first and second sections includes a channel portion for receiving the tailgate harness.

3. The harness assembly of claim 2, wherein each of the first and third sections include a generally L-shaped cross-sectioned low-profile portion.

4. The harness assembly of claim 1, wherein the first section and the second section are configured to secure the tailgate harness against the first portion of the tailgate frame and the third section is configured to secure the tailgate harness against the second portion of the tailgate frame.

5. The harness assembly of claim 1, wherein the protector includes a first attachment member and a second attachment member, the first and second attachment members mounting the protector to the tailgate frame.

6. The harness assembly of claim 5, wherein the first attachment member is generally clip-shaped for insertion through an opening located on the tailgate frame.

7. The harness assembly of claim 6, wherein first attachment member includes an arm and at least one spring-biased finger connected to an end of the arm, the at least one finger being biased away from the arm, the at least one finger being deflected towards the arm as the first attachment member is being inserted through the opening of the tailgate frame and springing away from the arm as the first attachment member is fully inserted through the opening of the tailgate frame.

8. The harness assembly of claim 5, wherein the second attachment member is generally hook-shaped, the second attachment member being mounted to a bottom edge of the tailgate frame.

9. The harness assembly of claim 1, further including a separate attachment device mounted to the vehicle body and configured to route the tailgate harness along the vehicle body.

10. The harness assembly of claim 9, further including an elongated tube for receiving a portion of the tailgate harness extending between the protector and the attachment device, the tube protecting the tailgate harness from damage.

11. A harness assembly for a vehicle including a vehicle body and a dual-mode tailgate connected to the vehicle body via a dual-action hinge configured to allow the tailgate to be selectively openable in a first, fold-down direction and a second, side-to-side direction, the harness assembly comprising:
a protector configured to route a tailgate harness from the tailgate under the dual-action hinge and to the vehicle body, the protector being mounted to a frame of the tailgate, the protector having a protector body including a first section laterally spaced from and extending generally parallel to an outboard lateral side of the tailgate frame and a second section extending generally perpendicular to the first section, each of the first and second sections including a channel portion for receiving the tailgate harness, and a third section extending angularly from the second section, each section of the protector body receiving the tailgate harness and routing the tailgate harness along the tailgate frame.

12. The harness assembly of claim 11, wherein each of the first and third sections include a generally planar portion which abuts a portion of the tailgate frame and a lip extending outwardly from the planar portion.

13. The harness assembly of claim 11, wherein the protector body integrally includes a first attachment member and a second attachment member configured to mount the protector to the tailgate frame.

14. The harness assembly of claim 13, wherein the first attachment member is clip-shaped for insertion through an opening located on the tailgate frame and the second attachment member is hook-shaped for mounting to a bottom edge of the tailgate frame.

15. The harness assembly of claim 11, further including a separate attachment device mounted to the vehicle body and configured to route the tailgate harness along the vehicle body and a corrugated tube for receiving a portion of the tailgate harness extending between the protector and the attachment device, the corrugated tube protecting the tailgate harness from damage.

16. A vehicle comprising:
a vehicle body;
a dual-mode tailgate having a frame;
a dual-action hinge configured to connect the dual-mode tailgate to the vehicle body and configured to allow the tailgate to be selectively openable in a first, fold-down direction and a second, side-to-side direction; and
a protector configured to route a tailgate harness from the tailgate under the dual-action hinge and to the vehicle body, the protector including:
a protector body including a first section laterally spaced from and extending generally parallel to an outboard lateral side of the frame of the tailgate, a second section extending generally perpendicular to the first section, and a third section extending angularly from the second section, and
a first attachment member and a second differing attachment member for mounting the protector to the tailgate frame.

17. The vehicle of claim 16, wherein the first section includes a generally L-shaped low-profile portion, the low-profile portion being positioned under the dual-action hinge.

18. The vehicle of claim 16, further including an attachment device mounted to the vehicle body and configured to route the tailgate harness along the vehicle body and a slit-less corrugated tube for receiving a portion of the tailgate harness extending between the protector and the attachment device, the corrugated tube protecting the tailgate harness from damage.

* * * * *